United States Patent
Kwon et al.

(10) Patent No.: US 10,358,412 B2
(45) Date of Patent: Jul. 23, 2019

(54) METHOD OF PREPARING DIFLUORINATED ALCOHOL COMPOUND

(71) Applicant: SAMHWA PAINTS INDUSTRIES CO., LTD., Ansan-si, Gyeonggi-do (KR)

(72) Inventors: Da Eun Kwon, Gunpo-si (KR); Myeng Chan Hong, Pyeongtaek-si (KR); Chong Yun Kwag, Seoul (KR)

(73) Assignee: Samhwa Paints Industries Co., Ltd., Ansan-si (KR)

( * ) Notice: Subject to any disclaimer, the term of this patent is extended or adjusted under 35 U.S.C. 154(b) by 78 days.

(21) Appl. No.: 15/239,523

(22) Filed: Aug. 17, 2016

(65) Prior Publication Data

US 2017/0313651 A1    Nov. 2, 2017

(30) Foreign Application Priority Data

Apr. 28, 2016  (KR) ........................ 10-2016-0052121

(51) Int. Cl.
| | |
|---|---|
| *C07C 253/30* | (2006.01) |
| *C07C 29/14* | (2006.01) |
| *C07C 41/26* | (2006.01) |
| *C07C 201/12* | (2006.01) |
| *C07C 29/64* | (2006.01) |

(52) U.S. Cl.
CPC ............ *C07C 253/30* (2013.01); *C07C 29/14* (2013.01); *C07C 29/64* (2013.01); *C07C 41/26* (2013.01); *C07C 201/12* (2013.01)

(58) Field of Classification Search
None
See application file for complete search history.

(56) References Cited

PUBLICATIONS

Grant & Hackh's Chemical Dictionary (5th Ed. 1987) at p. 148.*
Good et al., Optimized S-Trityl-L-cystein-Based Inhibitors of Kinesin Spindle Protein with Potent in Vivo Antitumor Activity in Lung Cancer Xenograft Models. Journal of Medicinal Chemistry, 2013, 56, 1878-1893.*
Altiti et al., An organocatalytic strategy for the stereoselective synthesis of C-galatosides with fluorine at the psudoanomeric carbon. Organic & Biomolecular Chemistry, 2015, 13, 10328-10335.*

* cited by examiner

*Primary Examiner* — Po-Chih Chen
(74) *Attorney, Agent, or Firm* — Nixon Peabody LLP

(57) ABSTRACT

A method of preparing a difluorinated alcohol compound is provided. The difluorinated alcohol compound can be easily synthesized when an aldehyde and N-fluorobenzenesulfonimide are reacted in the presence of L-proline, and thus the method has advantage in that preparation processes are simple and reagents are economical and safe, compared to the related-art methods. Therefore, the preparation method can be effectively applied to prepare a difluorinated alcohol used in various applications for raw materials such as functional medicines, agricultural chemicals, polymerizable compounds, etc.

15 Claims, No Drawings

METHOD OF PREPARING DIFLUORINATED ALCOHOL COMPOUND

CROSS-REFERENCE TO RELATED APPLICATION

This application claims priority to and the benefit of Korean Patent Application No. 2016-0052121, filed on Apr. 28, 2016, the disclosure of which is incorporated herein by reference in its entirety.

BACKGROUND

1. Field of the Invention

The present invention relates to a method of preparing a difluorinated alcohol compound, and more particularly, to a method of preparing a difluorinated alcohol compound used for raw materials such as functional medicines, agricultural chemicals, polymerizable compounds, etc. More particularly, the present invention relates to a method of preparing a difluorinated alcohol compound, which includes reacting an aldehyde and N-fluorobenzenesulfonimide (NFSI) in the presence of L-proline and reducing the reaction product using sodium borohydride.

2. Discussion of Related Art

Representative medicine containing fluorine atoms include fluorouracil used as an anti-cancer drug, fluoxetine used as an anti-depressant, ciprofloxacin known as an anti-anthrax drug, etc. In this way, the importance of fluorinated compounds has increased in the fields of pharmaceuticals, agricultural chemicals and material science. This is because that the fluorinated compounds have improved properties such as solubility, metabolic stability, lipophilicity, and the like when hydrogen is replaced with a fluorine atom. As a result, the research on synthesis of fluorinated organic compounds has been actively conducted.

The fluorinated alcohol contains fluorine atoms, and thus has features in that it has high polarity and acidity and is not easily oxidized. Therefore, the fluorinated alcohol has been used as a raw material for synthesizing functional medicines, agricultural chemicals, fluorine-containing polymerizable compounds, etc. Surfactants may be prepared through a phosphate reaction or prepared through an ethoxylate reaction after addition of ethylene oxide, or various water- or oil-repelling agents may be prepared through an esterification reaction. In this case, the functions of fluorine may be imparted to urethane through a urethane reaction with isocyanates. Such a fluorinated alcohol has come into the spotlight since it has achievable characteristics such as hydrophobicity, oil resistance, high thermal and chemical stability, low surface energy, low solubility in hydrocarbons, lubricity, releasability, etc.

Fluorinated paints have been known as super-weather-resistant paints, and have been mainly applied to installations or luxury apartment buildings which are difficult to maintain and repair due to their high level of price as non-contaminating paints that have very excellent physical properties and aids in maintaining the initial surface state of buildings. Also, the fluorinated paints have been applied to food processors and baking pans, or release agents for industries due to their properties such as water and oil repellency, etc.

Fluorinated alcohols such as $CF_3CH_2OH$ (TFE), $(CF_3)_2CHOH$ (HFIP), $HCF_2CF_2CH_2OH$ (TFP), $C_6F_{13}C_2H_4OH$, and the like have been put to practical use. In this case, TFE is of importance as a source material for inhalation anesthetics such as isoflurane and desflurane. Also, TFE has high thermal stability and dynamic characteristics, has been used for a working medium for Rankine cycle systems, for example, a medium for waste heat recovery power generation systems, has been used as a solvent for polymers such as polyamides, PMMA, acetylcellulose, etc., and has been used as a basic material for optical fibers when converted into monomers such as methacrylates.

HFIP has been used as a solvent of PET, polyamides, polyvinyl alcohol, and the like, particularly used as an eluent in a solution for GPC analysis, and is of importance as a resist when HFIP is introduced into the resist. When a substrate is coated with this resist, the resist exhibits high transparency and adhesion to the substrate in addition to hydrophilicity, and generally has high sensitivity when exposed to an argon fluoride (ArF) or krypton fluoride (KrF) light source with a wavelength of 300 nm or less, and thus has been used to prepare a radiation-sensitive resist polymer.

TFP has been used as a solvent in which, due to its nature of having no influence on the substrate, a pigment is dissolved and applied onto a polycarbonate substrate to form a recording layer for optical recording media.

$C_6F_{13}C_2H_4OH$ has been used as an oil-repelling agent for paper or a release agent when esterified with phosphoric acid. Also, the urethane compounds reacting with isocyanates have medically good stability in blood or tissue, and thus have emerged as an alternative to anti-fouling coatings and materials for high-pressure emulsification devices.

Medicines having a difluorinated structure have also been developed. In the prior art, these compounds have been used to remove agriculturally harmful pests such as bugs or mites, or used as an anthelmintic drug for mites or a pesticide for moths such as tobacco budworm, beetles such as Mexican bean beetle, etc.

Also, according to other prior art, there are β2 adrenergic receptor antagonists that work against congenital lung diseases such as asthma or bronchitis. Such medicines also have a difluorinated structure. The medicines have been used as therapeutic agents to treat premature labor, glaucoma, nerve disorders, cardiac disorders, etc. in addition to the lung diseases.

According to a first related art method, 2,2-difluoro-2-(4-fluorophenyl)ethanol which is an alcohol into which two fluorine atoms are introduced is synthesized through three steps. 1-Bromo-4-fluorobenzene and diethyl oxalate are subjected to a Grignard reaction at −78° C. in the presence of magnesium to obtain ethyl(4-fluorobenzoyl)formate with a yield of 44%, and 2-(4-fluorophenyl)-2,2-difluoroethyl ether acetate is obtained at 60° C. with a yield of 52% using diethylaminosulfur trifluoride (DAST). As a final compound, 2,2-difluoro-2-(4-fluorophenyl)ethanol is synthesized with a yield of 75% using sodium borohydride as a reducing agent.

According to a second related art method, 2,2-difluoro-2-phenylethanol which is an alcohol into which two fluorine atoms are introduced is synthesized through five steps. N-bromosuccinimide (NBS) and triethylamine trihydrofluoride (TEA-3HF) are reacted at room temperature for 15 hours to synthesize (2-bromo-1-fluoroethyl)benzene from styrene, and 1-(fluorovinyl)benzene is synthesized in the presence of a solvent, tetrahydrofuran, using potassium tert-butoxide. Then, (2-bromo-1,1-difluoroethyl)benzene is obtained using NBS and TEA-3HF, and potassium acetate and 18-Crown-6 are reacted at 150° C. for 15 hours in the presence of a dimethylformamide solvent to synthesize 2,2-difluoro-2-phenylethyl acetate. As a final compound, 2,2-difluoro-2-phenylethanol is synthesized using sodium hydroxide.

According to a third related art method, (2,2-difluoro-3-(4-propylphenyl)propan-1-ol) which is an alcohol into which two fluorine atoms are introduced is synthesized through four steps. 2,2-Difluoro-3-hydroxy-3-(4-propylphenyl)propanoate is synthesized using ethylbromodifluoroacetate and 4-propylbenzaldehyde, and 2,2-difluoro-3-(((methylthio)carbonothioyl)oxy)-3-(4-propylphenyl)propanoate is obtained using 1,8-diazabicyclo[5.4.0]undec-7-ene (DBU) and carbon disulfide (CS$_2$). Tributyltin hydride and azobisisobutyronitrile (AIBN) are added in the presence of a toluene solvent and refluxed to synthesize 2,2-difluoro-3-(4-propylphenyl)propanoate, and 2,2-difluoro-3-(4-propylphenyl)propan-1-ol is synthesized as a final compound using lithium aluminum hydride as a reducing agent.

SUMMARY OF THE INVENTION

The first related art method has drawbacks in that the synthesis is carried out with a relatively low yield through the three steps, a magnesium metal and an expensive diethylaminosulfur trifluoride reagent are used, and the reaction is carried out at an extremely low temperature (−78° C.) or a high temperature (60° C.).

The second related art method has drawbacks in that the synthesis is carried out through the five steps, the expensive 18-Crown-6 is used, and the reaction is carried out at a high temperature (150° C.) for a long period of time.

The third related art method has drawbacks in that the synthesis is carried out through the four steps, zinc and tin metals and a carbon disulfide reagent having strong toxicity are used, and the reaction is dangerous due to the use of lithium aluminum hydride exhibiting violent reactivity. Also, it has a drawback in that it is uneconomical since a reflux process and 1,8-diazabicyclo[5.4.0]undec-7-ene are used.

The above-described related art methods have problems in that the methods are uneconomical and not safe due to the use of an expensive reagent and complicated synthesis process, and the reaction is carried out at a high temperature or an extremely low temperature.

According to an aspect of the present invention, there is provided a method of preparing a difluorinated alcohol, characterized in that the method includes reacting an aldehyde and N-fluorobenzenesulfonimide.

According to another aspect of the present invention, there is provided a method of preparing a difluorinated alcohol, characterized in that the method includes reacting the aldehyde and the N-fluorobenzenesulfonimide in the presence of L-proline.

According to still another aspect of the present invention, there is provided a method of preparing a difluorinated alcohol, characterized in that the aldehyde is represented by the following Formula 1:

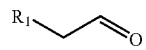

Formula 1 wherein R$_1$ represents any one selected from the group consisting of an unsubstituted C$_1$ to C$_{20}$ alkyl group, a substituted C$_1$ to C$_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group.

According to yet another aspect of the present invention, there is provided a method of preparing a difluorinated alcohol, characterized in that R$_1$ in Formula 1 is an unsubstituted phenyl group, or a phenyl group substituted with —OCH$_3$, —CH$_3$, —F, —Cl, —Br, —CF$_3$, —CN, or —NO$_2$.

According to yet another aspect of the present invention, there is provided a method of preparing a difluorinated alcohol, characterized in that the aldehyde is represented by the following Formula 2:

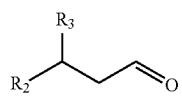

Formula 2 wherein R$_2$ represents any one selected from the group consisting of an unsubstituted C$_1$ to C$_{20}$ alkyl group, a substituted C$_1$ to C$_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and R$_3$ represents any one selected from the group consisting of a hydrogen atom, an unsubstituted C$_1$ to C$_{20}$ alkyl group, and a substituted C$_1$ to C$_{20}$ alkyl group.

According to yet another aspect of the present invention, there is provided a method of preparing a difluorinated alcohol, characterized in that R$_2$ in Formula 2 is an unsubstituted phenyl group, or a phenyl group substituted with —OCH$_3$, —CH$_3$, —F, —Cl, —Br, —CF$_3$, —CN, or —NO$_2$, and R$_3$ is a hydrogen atom, —CH$_3$, or C$_2$H$_5$.

According to yet another aspect of the present invention, there is provided a method of preparing a difluorinated alcohol, characterized in that the aldehyde is represented by the following Formula 3:

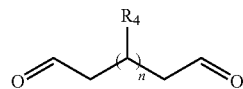

Formula 3 wherein R$_4$ represents any one selected from the group consisting of an unsubstituted C$_1$ to C$_{20}$ alkyl group, a substituted C$_1$ to C$_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and n is in a range of 1 to 20.

According to yet another aspect of the present invention, there is provided a method of preparing a difluorinated alcohol, characterized in that the difluorinated alcohol is represented by the following Formula 4:

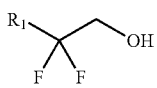

Formula 4 wherein R$_1$ represents any one selected from the group consisting of an unsubstituted C$_1$ to C$_{20}$ alkyl group, a substituted C$_1$ to C$_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group.

According to yet another aspect of the present invention, there is provided a method of preparing a difluorinated alcohol, characterized in that $R_1$ in Formula 4 is an unsubstituted phenyl group, or a phenyl group substituted with —$OCH_3$, —$CH_3$, —F, —Cl, —Br, —$CF_3$, —CN, or —$NO_2$.

According to yet another aspect of the present invention, there is provided a method of preparing a difluorinated alcohol, characterized in that the difluorinated alcohol is represented by the following Formula 5:

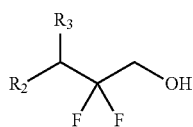

Formula 5 wherein $R_2$ represents any one selected from the group consisting of an unsubstituted $C_1$ to $C_{20}$ alkyl group, a substituted $C_1$ to $C_{20}$ alkyl group, an unsubstituted heterocyclic group, a substituted heterocyclic group, an unsubstituted phenyl group, a substituted phenyl group, an unsubstituted cyclohexyl group, and a substituted cyclohexyl group, and $R_3$ represents any one selected from the group consisting of a hydrogen atom, an unsubstituted $C_1$ to $C_{20}$ alkyl group, and a substituted $C_1$ to $C_{20}$ alkyl group.

According to yet another aspect of the present invention, there is provided a method of preparing a difluorinated alcohol, characterized in that $R_2$ in Formula 5 is an unsubstituted phenyl group, or a phenyl group substituted with —$OCH_3$, —$CH_3$, —F, —Cl, —Br, —$CF_3$, —CN, or —$NO_2$, and $R_3$ is a hydrogen atom, —$CH_3$, or $C_2H_5$.

According to yet another aspect of the present invention, there is provided a method of preparing a difluorinated alcohol, characterized in that the difluorinated alcohol is represented by the following Formula 6:

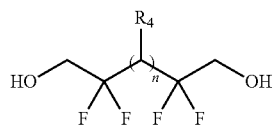

Formula 6 wherein $R_4$ represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and n is in a range of 1 to 20.

According to yet another aspect of the present invention, there is provided a method of preparing a difluorinated alcohol, characterized in that the method further includes adding sodium borohydride after the reaction of the aldehyde and the N-fluorobenzenesulfonimide (NFSI).

According to yet another aspect of the present invention, there is provided a method of preparing a difluorinated alcohol, characterized in that the addition of the sodium borohydride includes stirring reaction mixture at room temperature for 1 to 6 hours.

According to yet another aspect of the present invention, there is provided a method of preparing a difluorinated alcohol, characterized in that the reaction temperature is in a range of 0° C. to 100° C.

According to yet another aspect of the present invention, there is provided a method of preparing a difluorinated alcohol, characterized in that the reaction time is in a range of 2 hours to 24 hours.

DETAILED DESCRIPTION OF EXEMPLARY EMBODIMENTS

Exemplary embodiments of the present invention will be described in detail below. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclature used in this specification and the experimental methods described below are widely known and generally used in the related art.

The method of preparing a difluorinated alcohol according to one exemplary embodiment of the present invention may include reacting an aldehyde and a fluorine-containing compound.

NF-based reagents such as N-fluorobenzenesulfonimide, SELECTFLUOR® (1-(chloromethyl)-4-fluoro-1,4-diazoniabicyclo[2.2.2]octane ditetrafluoroborate), 1-fluoro-4-hydroxy-1,4-diazabicyclo[2.2.2]octane bis(tetrafluoroborate) (NFTh), N-fluoropyridinium pyridine heptafluorodiborate (NFPy), and the like may be used as the fluorine-containing compound. The use of N-fluorobenzenesulfonimide is most preferred since the N-fluorobenzenesulfonimide is inexpensive and has a high yield, and a small amount of byproducts are produced.

The reaction may be carried out using a reaction compound. Also, examples of the reaction compound that may be used herein may include L-proline, D-proline, (S)-α allyl-proline hydrochloride, (R)-pyrrolidine-2-carboxylic acid methyl ester, H-D-pro-O-ethyl hydrochloride, D-proline methyl ester hydrochloride, etc. The use of L-proline is most preferred since the L-proline has a high yield and is inexpensive.

When the aldehyde, the fluorine-containing compound, and the reaction compound are present at a ratio of 1:(2 to 4):(0.1 to 4), the yield may be highest, and byproducts may be produced at a slowly increasing rate. In particular, the ratio of the aldehyde, N-fluorobenzenesulfonimide and L-proline is most preferably in a range of 1:(2 to 4):(0.1 to 4). It is not desirable that each of the components is present in an amount less than in this molar ratio, as the yield may be lowered. On the other hand, in terms of economy, it is not preferred that each of the components is present in an amount greater than in this molar ratio, as byproducts may be produced.

In the method of preparing the difluorinated alcohol, a first solvent used in a fluorination reaction, and a second solvent used in a reduction reaction may be different from each other.

The first solvent is preferably used in the fluorination reaction. Polar aprotic solvents such as dimethylacetamide (DMAc), dimethylformamide (DMF), dimethylsulfoxide (DMSO), tetrahydrofuran (THF), acetonitrile (ACN), and the like may be used as the first solvent. The use of dimethylacetamide (DMAc) is most preferred in terms of high yield and less byproducts.

The second solvent is preferably used in the reduction reaction. Alcohol-based solvents such as methanol, ethanol, butanol, isopropanol, and the like may be used as the second solvent. The use of methanol is most preferred in terms of high yield.

A compound represented by the following Chemical Formula 1 may be used as the aldehyde, but a compound represented by the following Formula 1 is particularly preferred:

[Chemical Formula 1]

wherein R represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group; and

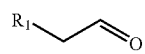

Formula 1 wherein $R_1$ may represent any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group.

Preferably, $R_1$ may be an unsubstituted phenyl group. Optionally, $R_1$ may be a phenyl group substituted with $OCH_3$, $CH_3$, F, Cl, Br, $CF_3$, CN, or $NO_2$.

More preferably, $R_1$ may be represented by one of the following Formulas.

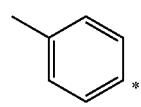 (R₁-1)

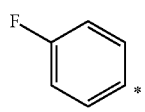 (R₁-2)

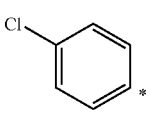 (R₁-3)

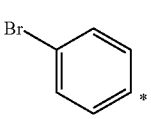 (R₁-4)

-continued

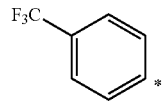 (R₁-5)

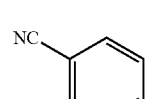 (R₁-6)

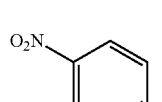 (R₁-7)

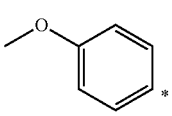 (R₁-8)

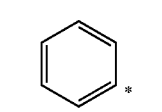 (R₁-9)

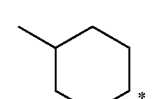 (R₁-10)

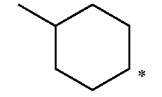 (R₁-11)

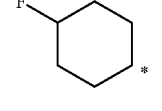 (R₁-12)

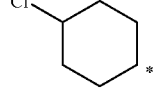 (R₁-13)

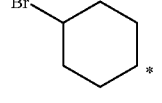 (R₁-14)

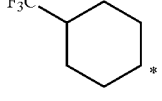 (R₁-15)

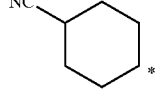 (R₁-16)

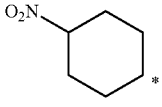 (R₁-17)

(R₁-18)

(wherein * represents a group used to link a residue of Formula 1-1 to the R₁ group.)

Formula 1-1

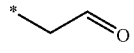

A compound represented by the following Formula 2 may be preferably used as the aldehyde:

Formula 2

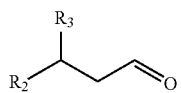

wherein $R_2$ may represent any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic grouped, an unsubstituted cyclohexyl group, and a substituted cyclohexyl group, and $R_3$ may represent any one selected from the group consisting of a hydrogen atom, an unsubstituted $C_1$ to $C_{20}$ alkyl group, and a substituted $C_1$ to $C_{20}$ alkyl group.

Preferably, an unsubstituted phenyl group may be used as $R_2$. Optionally, a phenyl group substituted with $OCH_3$, $CH_3$, F, Cl, Br, $CF_3$, CN, or $NO_2$ may be used as $R_2$. More preferably, a compound represented by one of the following Formulas may be used as $R_2$.

(R₂-1)

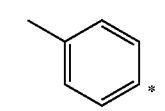

(R₂-2)

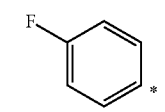

(R₂-3)

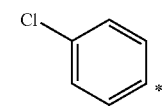

(R₂-4)

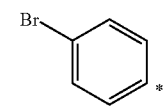

(R₂-5)

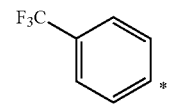

(R₂-6)

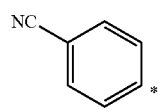

(R₂-7)

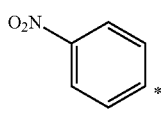

(R₂-8)

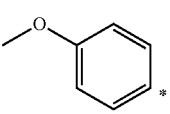

(R₂-9)

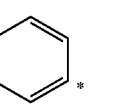

(R₂-10)

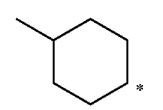

(R₂-11)

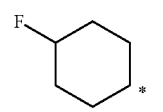

(R₂-12)

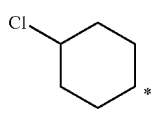

(R₂-13)

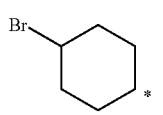

(R₂-14)

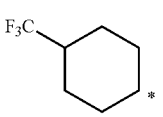

(R₂-15)

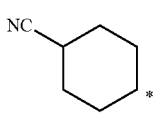

(R₂-16)

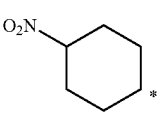

(R₂-17)

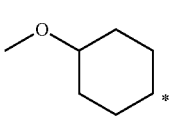

(R₂-18)

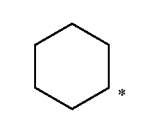

(wherein * represents a group used to link a residue of Formula 2-1 to the $R_2$ group.)

Formula 2-1

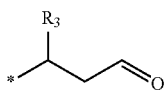

Preferably, a hydrogen atom, $CH_3$, or $C_2H_5$ may be used as $R_3$.

A compound represented by the following Formula 3 may be used as the aldehyde according to one exemplary embodiment of the present invention:

Formula 3

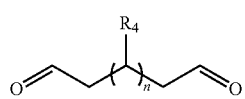

wherein $R_4$ represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and n is in a range of 1 to 20.

The compound prepared by the method of preparing a difluorinated alcohol according to one exemplary embodiment of the present invention may be represented by Formula 4:

Formula 4

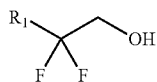

wherein $R_1$ represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group.

According to another exemplary embodiment of the present invention, $R_1$ in Formula 4 may be an unsubstituted phenyl group. Optionally, $R_1$ may be a phenyl group substituted with $OCH_3$, $CH_3$, F, Cl, Br, $CF_3$, CN, or $NO_2$.

More preferably, $R_1$ may be represented by one of the following Formulas.

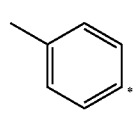 (R$_1$-1)

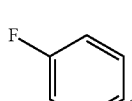 (R$_1$-2)

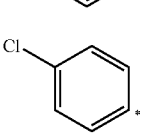 (R$_1$-3)

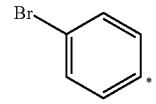 (R$_1$-4)

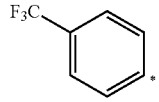 (R$_1$-5)

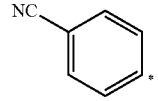 (R$_1$-6)

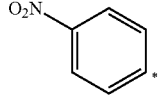 (R$_1$-7)

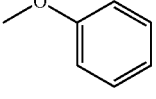 (R$_1$-8)

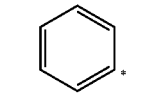 (R$_1$-9)

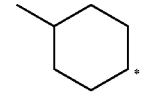 (R$_1$-10)

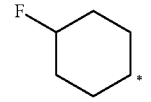 (R$_1$-11)

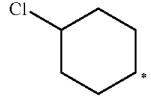 (R$_1$-12)

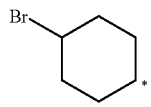 (R$_1$-13)

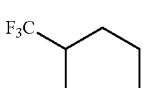 (R$_1$-14)

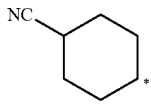 (R$_1$-15)

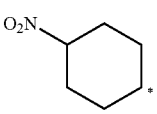 (R$_1$-16)

-continued

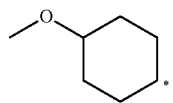
(R₁-17)

(R₁-18)

(wherein * represents a group used to link a residue of Formula 4-1 to the R₁ group.)

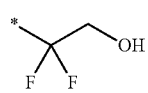
Formula 4-1

The compound prepared by the method of preparing a difluorinated alcohol according to one exemplary embodiment of the present invention may be represented by the following Formula 5:

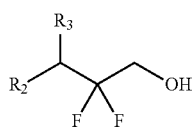
Formula 5 wherein $R_2$ may represent any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and $R_3$ may represent any one selected from the group consisting of a hydrogen atom, an unsubstituted $C_1$ to $C_{20}$ alkyl group, and a substituted $C_1$ to $C_{20}$ alkyl group.

Preferably, $R_2$ may be an unsubstituted phenyl group. Optionally, $R_2$ may be a phenyl group substituted with $OCH_3$, $CH_3$, F, Cl, Br, $CF_3$, CN, or $NO_2$. $R_3$ may be a hydrogen atom, $-CH_3$, or $C_2H_5$.

More preferably, a compound represented by one of the following Formulas may be used as $R_2$.

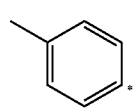
(R₂-1)

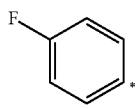
(R₂-2)

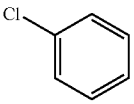
(R₂-3)

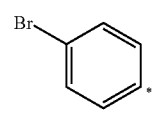
(R₂-4)

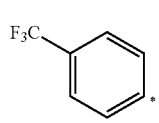
(R₂-5)

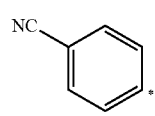
(R₂-6)

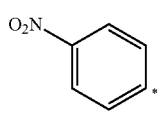
(R₂-7)

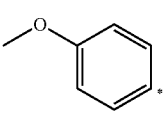
(R₂-8)

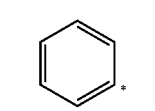
(R₂-9)

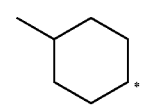
(R₂-10)

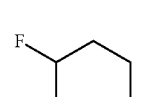
(R₂-11)

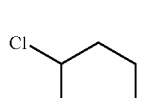
(R₂-12)

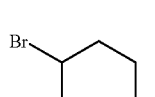
(R₂-13)

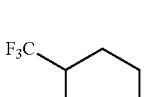
(R₂-14)

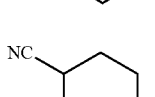
(R₂-15)

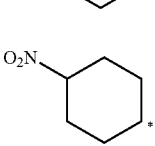
(R₂-16)

-continued

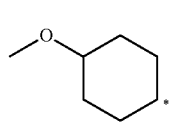
(R₂-17)

(R₂-18)

(wherein * represents a group used to link a residue of Formula 5-1 to the R₂ group.)

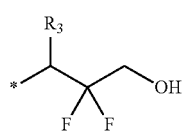
Formula 5-1

The difluorinated alcohol may be a compound represented by the following Formula 6:

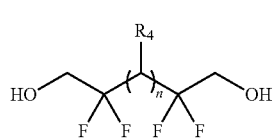
Formula 6 wherein R₄ represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and n is in a range of 1 to 20.

The method may further include adding sodium borohydride after the reaction of the aldehyde and the fluorine-containing compound.

Also, the addition of the sodium borohydride may include stirring reaction mixture at room temperature for 1 hour to 6 hours.

The temperature at which the aldehyde and the N-fluorobenzenesulfonimide are reacted may be in a range of 0° C. to 100° C. When the reaction temperature is less than 0° C., a lot of time may be required for the reaction, and the yield may be low. On the other hand, when the reaction temperature is greater than 100° C., the reaction byproducts may rapidly increase. Preferably, the reaction temperature may be room temperature.

Also, the reaction time may be in a range of 1 hour to 24 hours.

When the reaction time is shorter than 1 hour, the yield may be very low. On the other hand, when the reaction time is longer than 24 hours, the reaction byproducts may increase. Preferably, the reaction time may be in a range of 1 hour to 6 hours.

Example 1: Preparation of β,β-difluorobenzenepropanol 50 g of 3-phenylpropionaldehyde, 13 g of L-proline, and 250 mL of dimethylacetamide were put into a 1,000-mL reactor equipped with a stirring apparatus, and stirred at room temperature for 30 minutes. 235 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 62 g of sodium borohydride was added. After the temperature was warmed to room temperature, the resulting mixture was stirred for 2 hours. When the reaction was completed, a layer was separated to obtain β,β-difluorobenzenepropanol with a yield of 86%.

Example 2: Preparation of 2,2-difluoro-2-phenylethanol 50 g of phenylacetaldehyde, 14 g of L-proline, and 250 mL of dimethylacetamide were put into a 1,000-mL reactor equipped with a stirring apparatus, and stirred at room temperature for 30 minutes. 262 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 83 g of sodium borohydride was added. After the temperature was warmed to room temperature, the resulting mixture was stirred for 2 hours. When the reaction was completed, a layer was separated to obtain 2,2-difluoro-2-phenylethanol with a yield of 72%.

Example 3: Preparation of 2,2-difluoro-2-(4-methoxyphenyl)ethanol 50 g of 2-(4-methoxyphenyl)acetaldehyde, 11 g of L-proline, and 250 mL of dimethylacetamide were put into a 1,000-mL reactor equipped with a stirring apparatus, and stirred at room temperature for 30 minutes. 209 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 56 g of sodium borohydride was added. After the temperature was warmed to room temperature, the resulting mixture was stirred for 2 hours. When the reaction was completed, a layer was separated to obtain 2,2-difluoro-2-(4-methoxyphenyl)ethanol with a yield of 90%.

Example 4: Preparation of 2,2-difluoro-2-(4-methylphenyl)ethanol 50 g of 2-(4-methylphenyl)acetaldehyde, 13 g of L-proline, and 250 mL of dimethylacetamide were put into a 1,000-mL reactor equipped with a stirring apparatus, and stirred at room temperature for 30 minutes. 235 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 96 g of sodium borohydride was added. After the temperature was warmed to room temperature, the resulting mixture was stirred for 2 hours. When the reaction was completed, a layer was separated to obtain 2,2-difluoro-2-(4-methylphenyl)ethanol with a yield of 83%.

Example 5: Preparation of 2,2-difluoro-2-(4-fluorophenyl)ethanol 50 g of 2-(4-fluorophenyl)acetaldehyde, 12 g of L-proline, and 250 mL of dimethylacetamide were put into a 1,000-mL reactor equipped with a stirring apparatus, and stirred at room temperature for 30 minutes. 228 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 76 g of sodium borohydride was added. After the temperature was warmed to room temperature, the resulting mixture was stirred for 2 hours. When the reaction was completed, a layer was separated to obtain 2,2-difluoro-2-(4-fluorophenyl)ethanol with a yield of 68%.

Example 6: Preparation of 2,2-difluoro-2-(4-chlorophenyl)ethanol 50 g of 2-(4-chlorophenyl)acetaldehyde, 11 g of L-proline, and 250 mL of dimethylacetamide were put into a 1,000-mL reactor equipped with a stirring apparatus, and stirred at room temperature for 30 minutes. 204 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 75 g of sodium borohydride was added. After the temperature was warmed to room temperature, the resulting mixture was stirred for 2 hours. When the reaction was completed, a layer was separated to obtain 2,2-difluoro-2-(4-chlorophenyl)ethanol with a yield of 69%.

Example 7: Preparation of 2,2-difluoro-2-(4-bromophenyl)ethanol 50 g of 2-(4-bromophenyl)acetaldehyde, 8 g of L-proline, and 250 mL of dimethylacetamide were put into a 1,000-mL reactor equipped with a stirring apparatus, and stirred at room temperature for 30 minutes. 158 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 39 g of sodium borohydride was added. After the temperature was warmed to room temperature, the resulting mixture was stirred for 2 hours. When the reaction was completed, a layer was separated to obtain 2,2-difluoro-2-(4-bromophenyl)ethanol with a yield of 67%.

Example 8: Preparation of 2,2-difluoro-2-(4-trifluoromethylphenyl)ethanol 50 g of 2-(4-trifluoromethylphenyl)acetaldehyde, 9 g of L-proline, and 250 mL of dimethylacetamide were put into a 1,000-mL reactor equipped with a stirring apparatus, and stirred at room temperature for 30 minutes. 167 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 54 g of sodium borohydride was added. After the temperature was warmed to room temperature, the resulting mixture was stirred for 2 hours. When the reaction was completed, a layer was separated to obtain 2,2-difluoro-2-(4-trifluoromethylphenyl)ethanol with a yield of 60%.

Example 9: Preparation of 2,2-difluoro-2-(4-cyanophenyl)ethanol 50 g of 2-(4-cyanophenyl)acetaldehyde, 12 g of L-proline, and 250 mL of dimethylacetamide were put into a 1,000-mL reactor equipped with a stirring apparatus, and stirred at room temperature for 30 minutes. 217 g of N-fluorobenzenesulfonimide was added thereto, and stirred at room temperature for 4 hours. When the reaction was completed water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 67 g of sodium borohydride was added. After the temperature was warmed to room temperature, the resulting mixture was stirred for 2 hours. When the reaction was completed, a layer was separated to obtain 2,2-difluoro-2-(4-cyanophenyl)ethanol with a yield of 58%.

Example 10: Preparation of 2,2-difluoro-2-(4-nitrophenyl)ethanol 50 g of 2-(4-nitrophenyl)acetaldehyde, 10 g of L-proline, and 250 mL of dimethylacetamide were put into a 1,000-mL reactor equipped with a stirring apparatus, and stirred at room temperature for 30 minutes. 191 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 62 g of sodium borohydride was added. After the temperature was warmed to room temperature, the resulting mixture was stirred for 2 hours. When the reaction was completed, a layer was separated to obtain 2,2-difluoro-2-(4-nitrophenyl)ethanol with a yield of 57%.

Example 11: Preparation of β-difluoro-γ-methylbenzene propanol 50 g of 3-phenyl butyl aldehyde, 11 g of L-proline, and 250 mL of dimethylacetamide were put into a 1,000-mL reactor equipped with a stirring apparatus, and stirred at room temperature for 30 minutes. 213 g of N-fluorobenzenesulfonimide was added thereto, and stirred at room temperature for 4 hours. When the reaction was completed, water and organic solvent were added to chemical compound containing the aldehyde, the L-proline and the dimethylacetamide. Since then, water layer and organic solvent layer containing the chemical compound was produced. Under depressurization, the organic solvent layer of the layers was separated. In sequence, the organic solvent was removed from the organic solvent layer and then residue of the organic solvent layer was dissolved in 250 mL of methanol. After the temperature was reduced to 0° C., 36 g of sodium borohydride was added. After the temperature was warmed to room temperature, the resulting mixture was stirred for 2 hours. When the reaction was completed, a layer was separated to obtain β-difluoro-γ-methylbenzene propanol with a yield of 80%.

Accordingly, to improve the problems of the prior-art methods which are uneconomical due to the use of an expensive reagent and complicated synthesis process, the present inventors have simply synthesized a difluorinated alcohol by reacting N-fluorobenzenesulfonimide and an aldehyde in the presence of L-proline.

Since such a difluorinated alcohol compound can be introduced as a pharmaceutical intermediate, and can be prepared through a one-step process. As a result, a conventional multi-step complicated synthesis process can be simplified, thereby reducing production costs without using an additional reagent or requiring a production process. Owing to these characteristics, the method of the present invention is suitable for mass producing the difluorinated alcohol.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

What is claimed is:

1. A method of preparing a difluorinated alcohol, comprising reacting an aldehyde and a fluorine-containing compound,
wherein the fluorine-containing compound is any one selected from the group consisting of N-fluorobenzenesulfonimide, 1-(chloromethyl)-4-fluoro-1,4-diazonibicyclo[2.2.2]octane ditetrafluoroborate, 1-fluoro-4-hydroxy-1,4-diazabicyclo[2.2.2]octane bis(tetrafluoroborate) (NFTh), and N-fluoropyridinium pyridine heptafluorodiborate (NFPy), and
wherein the aldehyde is represented by the following Formula 1:

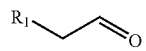

Formula 1 wherein $R_1$ is an unsubstituted phenyl group, or a phenyl group substituted with —$OCH_3$, —$CH_3$, —F, —Cl, —Br, —$CF_3$, —CN, or —$NO_2$.

2. The method of claim 1, wherein the reaction of the aldehyde and the fluorine-containing compound is performed in the presence of any one compound selected from the group consisting of L-proline, D-proline, (S)-α allyl-proline hydrochloride, (R)-pyrrolidine-2-carboxylic acid methyl ester, (R)-Ethyl pyrrolidine-2-carboxylate Hydrochloride, and D-proline methyl ester hydrochloride.

3. The method of claim 1, wherein the difluorinated alcohol is represented by the following Formula 4:

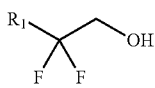

Formula 4 wherein $R_1$ is an unsubstituted phenyl group, or a phenyl group substituted with —$OCH_3$, —$CH_3$, —F, —Cl, —Br, —$CF_3$, —CN, or —$NO_2$.

4. The method of claim 1, further comprising:
adding sodium borohydride after the reaction of the aldehyde and the fluorine-containing compound.

5. The method of claim 4, wherein the addition of the sodium borohydride comprises stirring at room temperature for 1 hour to 6 hours.

6. The method of claim 1, wherein temperature is in a range of 0° C. to 100° C.

7. The method of claim 1, wherein reaction time is in a range of 2 hours to 24 hours.

8. A method of preparing a difluorinated alcohol, comprising
reacting an aldehyde and a fluorine-containing compound,
wherein the fluorine-containing compound is any one selected from the group consisting of N-fluorobenzenesulfonimide, 1-(chloromethyl)-4-fluoro-1,4-diazoniabicyclo[2.2.2]octane ditetrafluoroborate, 1-fluoro-4-hydroxy-1,4-diazabicyclo[2.2.2]octane bis(tetrafluoroborate) (NFTh), and N-fluoropyridinium pyridine heptafluorodiborate (NFPy), and
wherein the aldehyde is represented by the following Formula 2:

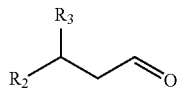

Formula 2 wherein $R_2$ is an unsubstituted phenyl group, or a phenyl group substituted with —$OCH_3$, —$CH_3$, —F, —Cl, —Br, —$CF_3$, —CN, or —$NO_2$, and $R_3$ is a hydrogen atom, —$CH_3$, or $C_2H_5$.

9. The method of claim 8, wherein the difluorinated alcohol is represented by the following Formula 5:

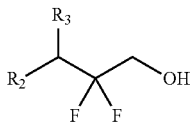

Formula 5 wherein $R_2$ is an unsubstituted phenyl group, or a phenyl group substituted with —$OCH_3$, —$CH_3$, —F, —Cl, —Br, —$CF_3$, —CN, or —$NO_2$, and $R_3$ is a hydrogen atom, —$CH_3$, or $C_2H_5$.

10. A method of preparing a difluorinated alcohol, comprising
reacting an aldehyde and a fluorine-containing compound,
wherein the fluorine-containing compound is any one selected from the group consisting of N-fluorobenzenesulfonimide, 1-(chloromethyl)-4-fluoro-1,4-diazoniabicyclo[2.2.2]octane ditetrafluoroborate, 1-fluoro-4-hydroxy-1,4-diazabicyclo[2.2.2]octane bis(tetrafluoroborate) (NFTh), and N-fluoropyridinium pyridine heptafluorodiborate (NFPy), and
wherein the aldehyde is represented by the following Formula 3:

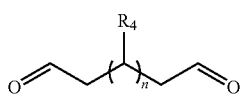

Formula 3 wherein $R_4$ represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and n is in a range of 1 to 20.

11. The method of claim 10, wherein the difluorinated alcohol is represented by the following Formula 6:

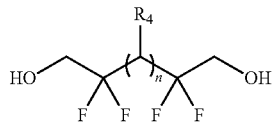

Formula 6 wherein $R_4$ represents any one selected from the group consisting of an unsubstituted $C_1$ to $C_{20}$ alkyl group, a substituted $C_1$ to $C_{20}$ alkyl group, an unsubstituted phenyl group, a substituted phenyl group, an unsubstituted heterocyclic group, a substituted heterocyclic group, an unsubstituted cyclohexyl group, and a substituted cyclohexyl group, and n is in a range of 1 to 20.

12. A method of preparing a difluorinated alcohol, comprising
reacting an aldehyde and a fluorine-containing compound to give a reaction product and reducing the reaction product to give the difluorinated alcohol,
wherein the fluorine-containing compound is any one selected from the group consisting of N-fluorobenzenesulfonimide, 1-(chloromethyl)-4-fluoro-1,4-diazoniabicyclo[2.2.2]octane ditetrafluoroborate, 1-fluoro-4-hydroxy-1,4-diazabicyclo[2.2.2]octane bis(tetrafluoroborate) (NFTh), and N-fluoropyridinium pyridine heptafluorodiborate (NFPy),
a first solvent is used in fluorination reaction,
a second solvent is used in reduction reaction, and
the first solvent and the second solvent are different from each other; and
wherein the aldehyde is represented by the following Formula 1:

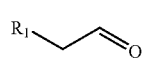

Formula 1 wherein $R_1$ is an unsubstituted phenyl group, or a phenyl group substituted with —$OCH_3$, —$CH_3$, —F, —Cl, —Br, —$CF_3$, —CN, or —$NO_2$.

13. The method of claim 12, wherein the reaction of the aldehyde and the fluorine-containing compound is performed in the presence of any one compound selected from the group consisting of L-proline, D-proline, (S)-α allylproline hydrochloride, (R)-pyrrolidine-2-carboxylic acid methyl ester, (R)-Ethyl pyrrolidine-2-carboxylate Hydrochloride, and D-proline methyl ester hydrochloride.

14. The method of claim 12, wherein the first solvent used in the fluorination reaction comprises any one compound selected from the group consisting of dimethylacetamide (DMAc), dimethylformamide (DMF), dimethylsulfoxide (DMSO), tetrahydrofuran (THF), and acetonitrile (ACN).

15. The method of claim 14, wherein the second solvent used in the reduction reaction comprises any one compound selected from the group consisting of methanol, ethanol, butanol, and isopropanol.

* * * * *